United States Patent [19]

Thomas et al.

[11] Patent Number: 4,859,802

[45] Date of Patent: Aug. 22, 1989

[54] PROCESS FOR REMOVING CONTAMINANTS FROM DIALKYL ETHERS OF POLYALKYLENE GLYCOLS

[75] Inventors: Eugene R. Thomas; Robert E. Steele, both of Houston, Tex.

[73] Assignee: Exxon Production Research Company, Houston, Tex.

[21] Appl. No.: 163,929

[22] Filed: Mar. 4, 1988

[51] Int. Cl.$^4$ ............................................. C07C 37/72
[52] U.S. Cl. ..................................................... 568/621
[58] Field of Search ............................................. 368/621

[56] References Cited

U.S. PATENT DOCUMENTS

| | | | |
|---|---|---|---|
| 3,030,426 | 4/1962 | Mosely et al. | 568/621 |
| 3,299,151 | 1/1967 | Wismer et al. | 568/621 |
| 3,492,358 | 1/1970 | Gurgiolo | 568/621 |
| 3,594,985 | 7/1971 | Ameen et al. | 55/44 |
| 3,737,392 | 6/1973 | Ameen et al. | 252/364 |
| 3,831,348 | 8/1974 | Pap | 55/73 |
| 4,334,102 | 6/1982 | Decker et al. | 568/621 |
| 4,395,385 | 7/1983 | Welsh | 423/234 |
| 4,404,098 | 9/1983 | Asdigian | 208/235 |
| 4,518,396 | 5/1985 | Rawson | 568/621 |
| 4,581,154 | 4/1986 | Kutsher et al. | 252/170 |
| 4,609,384 | 9/1986 | Ranke et al. | 55/40 |

*Primary Examiner*—Howard T. Mars
*Attorney, Agent, or Firm*—Gary D. Lawson; Pamela L. Wilson

[57] ABSTRACT

A process is described for removing contaminants from a contaminant-laden solution of dialkyl ethers of polyethylene glycols (polyether solvent) by mixing the solution with an aqueous base solution. The mixture produces at least two liquid phases of different densities, which are then separated from each other. The lighter liquid phase is predominantly the polyether solvent while the heavier liquid phase is predominantly the aqueous base solution and the contaminants. The process is particularly useful in removing triethylene glycol and other glycol-based dehydration solvents.

21 Claims, 1 Drawing Sheet

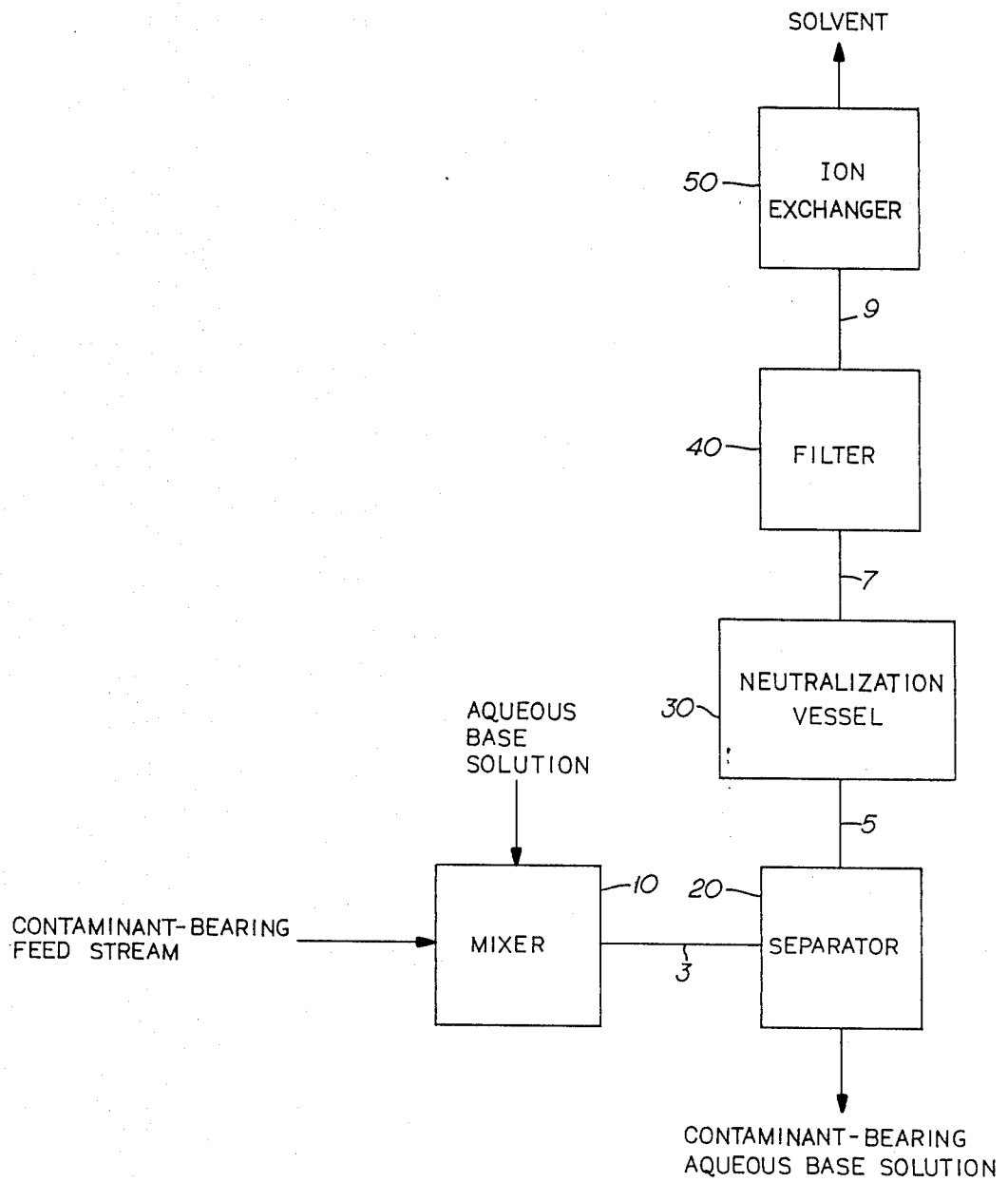

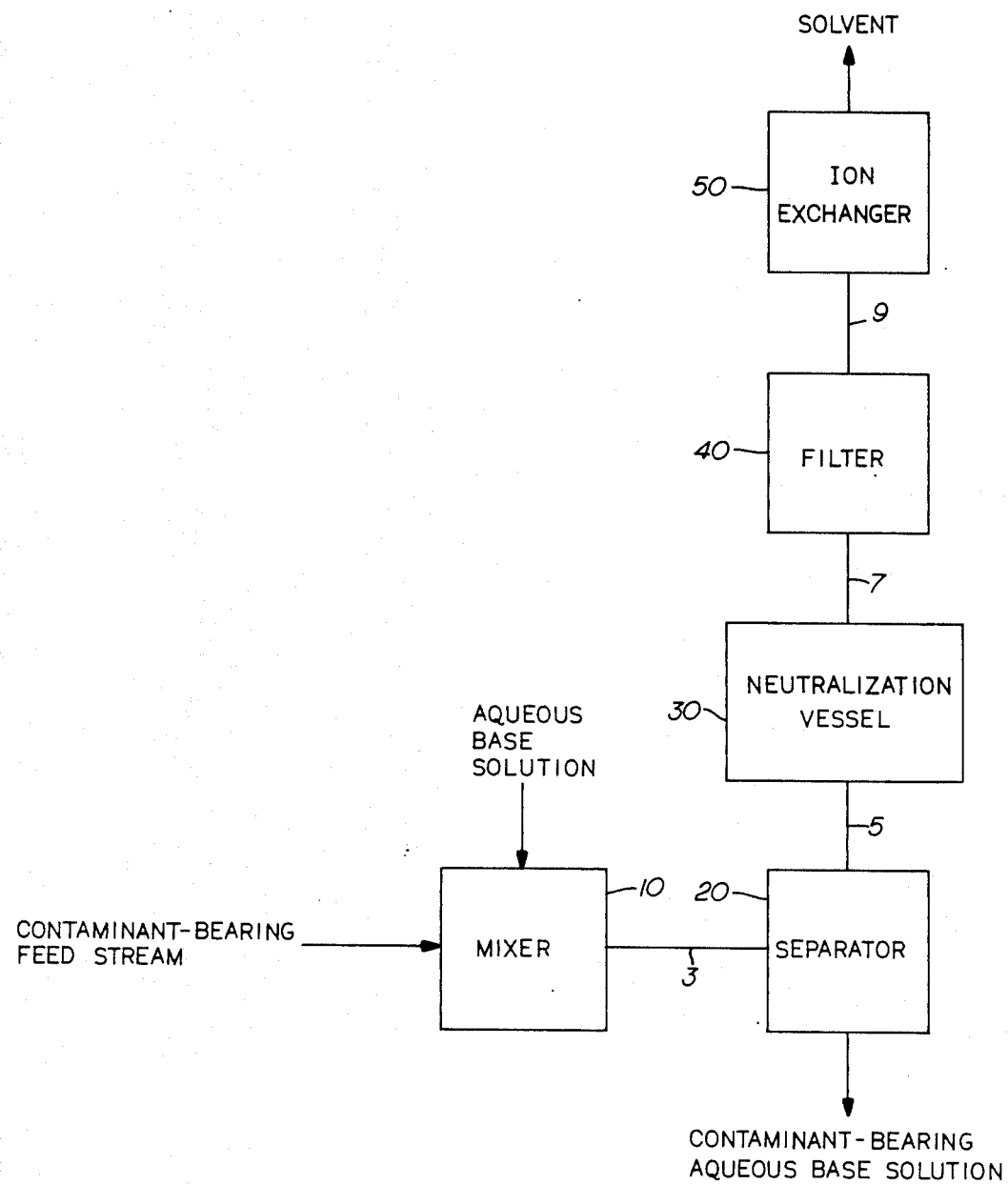

PROCESS FOR REMOVING CONTAMINANTS FROM DIALKYL ETHERS OF POLYALKYLENE GLYCOLS

FIELD OF THE INVENTION

This invention relates to a process for removing contaminants from dialkyl ethers of polyalkylene glycols. More specifically, it relates to an extraction process using an aqueous base solution to extract contaminants from a solution containing contaminants and dialkyl ethers of polyalkylene glycols.

BACKGROUND OF THE INVENTION

Natural gas that is produced from subterranean reservoirs usually contains mixtures of hydrocarbon gases (principally methane and ethane) and it may contain appreciable quantities of nonhydrocarbon gases (nitrogen, helium, water vapor, carbon dioxide and hydrogen sulfide). For efficient transportation and processing of the natural gas, it is frequently necessary to remove one or more of the nonhydrocarbon components.

Water vapor contained in natural gas is often removed from the gas in the vicinity of where the gas is produced so that the gas can be more economically and efficiently transported, stored and processed. If the water is not removed, if may accelerate pipeline and equipment corrosion and it may freeze or form hydrates and thereby plug pipelines, valves and orifices.

In a well known and commonly used process for dehydrating natural gas, the wet gas is contacted with a glycol such as triethylene glycol (TEG) in a countercurrent absorption column. Water vapor is absorbed by TEG as the gas flows up the absorption column countercurrent to the glycol flowing down the column. The TEG loaded with water is then heated to remove the water from it, and the lean TEG is recycled for mixing with wet gas in a continuous process. Although TEG has a low vapor pressure at temperatures typically used in this dehydration process, a small amount of TEG vaporizes or is entrained, thereby becoming a trace component of the natural gas mixture.

Acid gases (principally $CO_2$ and $H_2S$) present in the natural gas are removed to produce a "sweet" gas which will not interfere with further processing of the gas and will meet customer specifications. One process to remove acid gases from natural gas involves contacting the natural gas with a liquid solvent containing dialkyl ethers of polyalkylene glycol. One such polyether is the dimethyl ether of triethylene glycol. Mixtures of such polyether solvents are sold by Norton Company under the trademark SELEXOL ®.

In a process for removing acid gases from natural gas, the natural gas is mixed with a polyether solvent in a conventional countercurrent absorption column under superatmospheric conditions. The solvent absorbs most of the $H_2S$ and $CO_2$, and it absorbs essentially all of the triethylene glycol and other contaminants previously introduced into the gas. The solvent containing dissolved $H_2S$ and $CO_2$ may then be regenerated by flashing in a series of flashing steps, followed by stripping to remove $H_2S$, and then recycled to the top of the absorption column for reuse. For economic reasons, it is desirable to recycle as much of the solvent as possible, thereby minimizing the need to add fresh solvent.

One problem with recycling the polyether solvent is that contaminants such as triethylene glycol (from upstream dehydration) and corrosion inhibitors (used in the transportation of the gas through pipelines) accumulate during extensive recycling of the solvent. The accumulation of these contaminants may significantly reduce the efficiency of the solvent to remove acid gases. In addition, some of the contaminants may precipitate out of the solvent and deposit on process equipment such as pumps, piping and heat exchangers. This loss of efficiency can increase the operating expense of acid gas removal and it may decrease the gas capacity of the gas processing facility.

Distillation removal of triethylene glycol from polyether solvents such as SELEXOL ® is difficult because triethylene glycol has approximately the same vapor pressure as some of the components of SELEXOL ®.

There is a need for a simple process for removing contaminants from a polyether solvent to regenerate the solvent for longer usage. Removal of contaminants will reduce the need to periodically replace contaminated solvent with fresh solvent.

SUMMARY OF THE INVENTION

The present invention provides a process for removing contaminants from a solvent in which dialkyl ethers of polyalkylene glycols are the solvent's principal components. In this process, the solvent is mixed with an aqueous base solution. The mixture produces at least two liquid phases having different densities. The lighter phase contains solvent as the principal component and the heavier phase contains aqueous base solution and the contaminants as principal components. The lighter phase may be separated from the heavier phase using any conventional phase separation process. The lighter phase, substantially free of contaminants, may be used again without further treatment. However, if the lighter phase contains unwanted ions or particulates or if its pH is unacceptably high, the lighter phase may be further processed. Such further processing may include, but not limited to, centrifugation, neutralization, filtration, and ion exchange.

The base constituent of the aqueous base solution used in the process of this invention may be any base which when mixed with the solvent solution yields at least two phases having different densities. The pH of the aqueous solution should be higher than about 11 and preferably be higher than about 13. Sodium hydroxide is a preferred base.

The process of this invention is particularly useful in removing triethylene glycol from polyether solvents that are used for absorption of acid gases from feedstocks such as natural gas, synthetic natural gas, ammonium gas and refining gas.

BRIEF DESCRIPTION OF THE DRAWING

The Drawing is a block flow diagram illustrating one embodiment of practicing the process of this invention, and it is not intended to exclude from the scope of the invention other embodiments set out herein or which are the result of normal and expected modifications of this one specific embodiment. Various required subsystems such as pumps, valves, control systems and sensors have been deleted from the Drawing for the purposes of simplicity and clarity of presentation.

DESCRIPTION OF THE PREFERRED EMBODIMENTS

The present invention provides for the removal of contaminants from a solution containing the contaminants and dialkyl ethers of polyalkylene glycols. An aqueous base is mixed with the solution to induce the formation of one or more additional liquid phases having different densities. The lighter phase, comprising as a principal component dialkyl ethers of polyalkylene glycols, is then separated from the heavier phase(s).

The present invention is applicable to extraction of contaminants from polyether solvents represented by the formula:

$$R_1O(R_3)_xR_2 \quad \text{formula 1}$$

where $R_1$ and $R_2$ can be identical or different and each is a linear or branched-chain alkyl group, $R_3$ is an alkylene group having at least 2 carbon atoms, and x ranges from 1 to 10. Nonlimiting examples of suitable polyether solvents include dimethyl, diethyl, dipropyl and dibutyl ethers of ethylene, diethylene, triethylene, tetraethylene, pentaethylene, hexaethylene and heptaethylene glycols, and mixtures of such solvents. Particularly applicable solvents used in the process of this invention comprise mixtures of dialkyl ethers of polyalkylene glycols of the formula: $CH_3O(C_2H_4O)_xCH_3$ where x is in the range from 3 to 9.

In the practice of this invention the solvent may also contain minor amounts of hydrocarbons, carbon dioxide, hydrogen sulfide, and other compounds absorbed by the solvent in a gas absorption process. For convenience, a solvent solution containing as a principal component dialkyl ethers of polyalkylene glycols represented by formula 1 above will be designated herein as a "polyether solvent".

The aqueous base solution used in the process of this invention may comprise any water soluble compound which undergoes ionization in an aqueous solution to produce hydroxyl ions ($OH^-$) in considerable concentration. Preferred bases are water soluble alkali hydroxide compounds. Examples of suitable bases include ammonium hydroxide, alkaline metal hydroxides such as sodium hydroxide and potassium hydroxide, and alkaline earth hydroxides such as calcium hydroxide. Sodium hydroxide is particularly preferred because it tends to be less expensive and is generally more readily available than other strong bases.

The pH of the aqueous base solution used in this invention should be high enough to form at least two distinct phases when mixed with the polyether solvent. The inventors have observed that phase separation becomes less distinct as the pH of the aqueous base solution falls below about 11. The pH of the aqueous base solution should therefore be greater than about 11 and preferably greater than 13. An aqueous base solution containing from about 30 to 60 weight percent alkali metal hydroxide such as sodium hydroxide is suitable in practicing this invention.

The amount of base solution to mix with the polyether solvent can vary widely and will depend upon the amount of polyether solvent to be treated, the mixing time, and pH of the base solution. The amount of base solution should be sufficient to form at least two separate phases after mixing and sufficient to absorb the contaminants from the solvent. For illustration purposes only, a base to solvent ratio of about 1:100 to about 1:1, preferably about 1:25 to about 1:15, may be used.

Contaminants removed from the polyether solvent include polar compounds that are miscible in the aqueous base solution and compounds that react with the base to produce ionized solids or polar liquids. Polar liquids will generally be more miscible in the aqueous base solution than in the polyether solution. Ionized solids and polar liquids heavier than the polyether solution may be separated following mixing by conventional gravity separation techniques or filtration. Reaction precipitates that remain polyether solvent may be removed by filtration. Nonlimiting examples of contaminants that may be removed from a polyether solvent in accordance with this invention include alcohols such as methanol and ethanol, glycols such as triethylene glycol and diethylene glycol, and polar aromatic hydrocarbons such as phenol and aniline.

The process of this invention may be carried out within a wide range of temperatures and pressures. The pressures and temperatures should be selected that do not degrade the polyether solvent. Pressure-temperature relationships suitable in the practice of this invention are well understood by those skilled in the art, and need not be detailed herein.

Mixing of the solvent with the base solution is performed until intimate contact of the solvent and base have been effected. For purposes of illustration only, a mixing time of 1 minute to 5 minutes for mixing twenty liters of solvent with one liter of a sodium hydroxide solution should be sufficient.

The formation of multiple phases after mixing of a polyether solvent and an aqueous base and the preferential miscibility of certain contaminants may be due to a combination of phase behavior and chemical reaction phenomena. While not wishing to be bound by any particular theory, the following is offered as one explanation. Polyether solvents are generally slightly polar compounds that are highly miscible in water and most hydrocarbons. Polyether solvents are believed to be miscible in water because their ether groups hydrogen bond with the protons of water. Polar compounds such as triethylene glycol are miscible in water and polar organic solvents. When a polyether solvent is mixed with the aqueous base solution, the strong base reduces the number of protons in the aqueous solution that the solvent's ether groups can bond with, thus reducing the solvent's solubility in the aqueous base solution. On the other hand, a polar contaminate such as triethylene glycol stays in the aqueous solution since it reacts, ionizes, and/or hydrogen bonds with the base.

The process of the present invention may be better understood by referring to the Drawing, which is a block flow diagram illustrating one method of the present invention. A polyether solvent solution containing contaminants and an aqueous base solution enter a static mixer 10. The mixer 10 provides intimate mixing of the aqueous base solution and polyether solution. Although only one static mixer is shown in the Drawing, more than one may be used. The mixture then flows through line 3 to a separator 20 suitable for separating liquid phases having different densities. The phase separation may be performed in a batch or continuous process, and may be performed using a settling tank or a centrifuge. The heavier liquid phase(s), consisting predominantly of the contaminant-bearing aqueous base solution, is removed from the separator for further handling. Optionally, the contaminants may be removed from the base solution by processes well known to those skilled in the art so that the base can be reused in the process of this invention.

The lighter fluid phase, consisting predominantly of the polyether solvent, may be sent directly to a gas processing facility (not shown in the Drawing) for reuse. Depending on the solvent's intended use, it may be desirable to further treat the solvent to remove particulates, adjust the pH or remove alkali ions. Nonlimiting examples of further treatment include any one or more of the following: neutralization, filtration, centrifugation, and ion exchange. For example, a portion of the lighter phase may be filtered (or centrifuged) to remove solids, it may be neutralized to reduce the pH and then filtered, it may be deionized by any ion exchanger, or it may be neutralized, filtered and then deionized. The Drawing illustrates all of these additional treatments except centrifugation.

Referring again to the Drawing, at least a portion of the polyether solvent (the lighter phase) is sent from the separator 20 via line 5 to a neutralization vessel 30 to reduce the solvent's pH to a desired level. Reducing the solvent's pH to approximately the same pH as the contaminant-laden feed stream is preferred. Any convenient neutralizing agent may be used, including carbon dioxide and an aqueous acid.

The neutralized solvent is then passed through line 7 to a filter 40 for removal of solids. Particulates may have been present in the feed-solvent stream or they may have been formed as reaction byproducts during mixing of the base solution and contaminant-laden solvent and during neutralization of the solvent following mixing.

Following neutralization and filtration, if the polyether solvent solution still contains an unacceptably high alkali ion concentration, the solvent may be passed through line 9 to an ion exchanger 50 for further deionization. For example, if NaOH is used as a base, Na+ ions remaining in the solvent may be removed by the ion exchanger 50. The solvent leaving the ion exchanger will be essentially free of both contaminants and alkali ions.

All the steps of the present invention (mixing and separation and, optionally, neutralization, filtration and ion exchange) may be performed using conventional equipment. However, since the aqueous base solution is corrosive, the equipment should be made of corrosion resistant materials.

EXPERIMENTAL TEST

This invention is further illustrated by the following laboratory equipment, which demonstrates the operability of the invention and is not intended as limiting the scope of the invention as defined in the appended claims.

In this experiment, 174 grams of a solution containing 87.7 weight percent SELEXOL ®, 9.5 weight percent triethylene glycol and 2.8 weight percent water and other contaminants was thoroughly mixed with 15.4 grams of a 50 weight percent sodium hydroxide solution at 23° C. and atmospheric pressure. After mixing, the mixture split into two distinct liquid phases with 154.4 grams in the top (SELEXOL ® rich) phase. The two phases were separated by decantation and analyzed. The top phase contained about 96.5% of the original amount of the SELEXOL ®, and about 95% of the triethylene glycol has been removed. Compositions in weight percent of the two phases as measured by a gas chromatograph are presented in Table 1 below.

TABLE 1

| Component | Top Phase (wt %) | Bottom Phase (wt %) |
|---|---|---|
| SELEXOL ® | 98.0 | 0.4 |
| Triethylene glycol | 0.5 | 49.0 |
| Water & other contaminants | 1.5 | 50.6 |

The principle of the invention and the best mode contemplated for applying that principle have been described. It will be apparent to those skilled in the art that various changes may be made to the embodiments described above without departing from the spirit and scope of this invention as defined in the following claims. For example, additional equipment such as centrifuges, filters, and holding tanks may be introduced into the process for reasons of efficiency, economy, control or safety. It is, therefore, to be understood that this invention is not limited to the specific details shown and described.

What we claim is:

1. A process for removing a glycol from a solution of said glycol and a dialkyl ether of a polyalkylene glycol which comprises the steps of contacting said solution with an aqueous base solution in an amount and having a pH above about 11 so that said dialkyl ether of a polyethylene glycol and said aqueous base solution are substantially immiscible with each other, and recovering said dialkyl ether of a polyalkylene glycol.

2. The process of claim 1 wherein the glycol is diethylne glycol.

3. The process of claim 1 wherein the glycol is triethylene glycol.

4. The process of claim 1 wherein the dialkyl ether of polyalkylene glycol is selected from the formula $CH_3O(C_2H_4O)_xCH_3$ where x is in the range from 1 to 9.

5. The process of claim 1 wherein the ratio by volume of aqueous alkali hydroxide solution to dialkyl ether of a polyalkylene glycol ranges from 1:100 to 1:1.

6. The process of claim 5 wherein the ratio by volume of aqueous alkali hydroxide solution is dialkyl ether of a polyalkylene glycol ranges from 1:25 to 1:15.

7. The process of claim 1 wherein the aqueous base solution comprises alkali hydroxide.

8. The process of claim 7 wherein the alkali hydroxide is selected from the group consisting of sodium hydroxide, potassium hydroxide and ammonium hydroxide.

9. The process of claim 1 wherein the aqueous base solution has a pH higher than about 13.

10. A process for separating triethylene glycol from a solution comprising dialkyl ether of polyalkylene glycol as a principal component which comprises
    mixing said solution containing dialkyl ether of polyalkylene glycol with an aqueous alkaline solution in an amount and having a pH above about 11 so that said dialkyl ether of polyethylene glycol and said aqueous alkaline solution are substantially immiscible with each other, and forming at least two separate liquid phases having different densities, one phase comprising dialkyl ethers of polyalkylene glycols as a principal component and at least one other phase comprising alkaline solution as a principal component; and
    recovering the liquid phase comprising dialkyl ethers of polyalkylene glycols as a principal component.

11. A process for separating a glycol from a liquid polyether solvent containing said glycol, said polyether solvent containing predominantly dialkyl ethers of polyalkylene glycols, which comprises
   mixing said polyether solvent with an aqueous alkali hydroxide solution in an amount and having a pH above about 11 so that said dialkyl ether of polyethylene glycol and said aqueous alkali hydroxide solution are substantially immiscible with each other; and
   separating a first liquid phase comprising the polyether solvent as a principal component from a second liquid phase comprising the aqueous alkali hydroxide solution and glycol as principal components.

12. The process of claim 11 wherein said first liquid phase contains solids selected from the group consisting of feed-solvent stream particulates and reaction by-products, further comprising removing said solids from a portion of said first liquid phase.

13. The process of claim 12 wherein said solids are removed by filtering said portion of said first liquid phase.

14. The process of claim 12 wherein said solids are removed by centrifuging said portion of said first liquid phase.

15. The process of claim 11 further comprising contacting at least a portion of said first liquid phase with a neutralizing agent.

16. The process of claim 15 wherein the neutralizing agent is carbon dioxide.

17. The process of claim 15 wherein said first liquid phase contains solids selected from the group consisting of feed-solvent stream particulates and reaction by-products, further comprising removing said solids by filtering a portion of the first liquid phase.

18. The process of claim 11 wherein said first liquid phase contains alkali ions, further comprising removing said alkali ions from a portion of said first liquid phase by means of an ion exchanger.

19. The process of claim 11 further comprising contacting at least a portion of said first liquid phase with a neutralizing agent and, wherein said first liquid phase contains solids selected from the group consisting of feed-solvent stream particulates and reaction by-products, removing said solids from at least a portion of said first liquid phase which has been contacted by a neutralizing agent.

20. The process of claim 19 wherein said first liquid phase contains alkali ions, further comprising removing said alkali ions from at least a portion of said first liquid phase which has been contacted by the neutralizing agent by means of an ion exchanger.

21. A process for separating a glycol from a feed stream consisting essentially of the glycol and a polyether solvent comprising dialkyl ethers of polyalkylene glycols, which comprises the steps of:
   (a) contacting the feed stream with an aqueous alkali hydroxide solution in an amount and having a pH above about 11 so that said dialkyl ether of a polyethylene glycol and said aqueous alkali hyroxide solution are substantially immiscible with each other and having different densities;
   (b) separating a first liquid phase comprising the polyether solvent as a principal component from at least one other liquid phase comprising glycol-laden aqueous alkali hydroxide solution as a principal component;
   (c) contacting said first liquid with a neutralizing agent;
   (d) wherein said first liquid phase contains solids selected from the group consisting of feed-solvent stream particulates and reaction by-products, removing said solids from said first liquid phase; and
   (e) wherein said first liquid phase contains alkali ions, removing said alkali ions from said first liquid phase by means of an ion exchanger.

* * * * *